Figure 3:
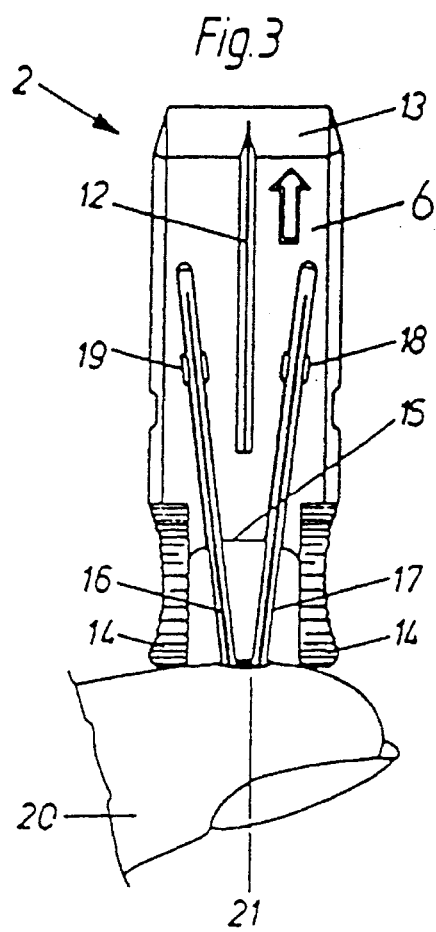

United States Patent [19]

Hauch et al.

[11] Patent Number: 5,567,869
[45] Date of Patent: Oct. 22, 1996

[54] METHOD AND APPARATUS FOR QUANTITATION OF RELEVANT BLOOD PARAMETERS

[75] Inventors: Ole Hauch, Hellerup; Jens B. Knudsen, Farum; Thomas M. Plum, Skodsborg, all of Denmark

[73] Assignee: Novo Nordisk A/S, Bagsvaerd, Denmark

[21] Appl. No.: 244,966

[22] PCT Filed: Dec. 18, 1992

[86] PCT No.: PCT/DK92/00382

§ 371 Date: Aug. 3, 1994

§ 102(e) Date: Aug. 3, 1994

[87] PCT Pub. No.: WO93/12422

PCT Pub. Date: Jun. 24, 1993

[30] Foreign Application Priority Data

Dec. 19, 1991 [DK] Denmark ................. 2031/91

[51] Int. Cl.⁶ .............. G01N 21/00; G01N 33/49; G01N 33/86
[52] U.S. Cl. ........... 73/64.410; 73/64.43; 73/61.65; 73/61.69; 422/73; 422/82.05; 436/70; 356/39; 128/637; 128/DIG. 22
[58] Field of Search ............... 73/64.41, 64.43, 73/61.65, 61.69; 422/73, 82.05; 436/69, 70; 435/13; 128/637, DIG. 22; 356/39

[56] References Cited

U.S. PATENT DOCUMENTS

| | | | |
|---|---|---|---|
| 3,307,392 | 3/1967 | Owen et al. | 73/64.43 |
| 3,458,287 | 7/1969 | Gross et al. | 73/64.43 |
| 3,814,585 | 6/1974 | Bailly | 73/64.43 |
| 3,923,397 | 12/1975 | Shuck | 356/39 |
| 4,011,142 | 3/1977 | Jacobi | 435/13 |
| 4,252,536 | 2/1981 | Kishimoto et al. | 73/64.43 |
| 4,303,336 | 12/1981 | Cullis | 356/39 |
| 4,848,900 | 7/1989 | Kuo et al. | 356/39 |
| 5,188,940 | 2/1993 | Krause et al. | 436/69 |
| 5,298,224 | 3/1994 | Plum | 73/64.43 |
| 5,350,676 | 9/1994 | Oberhardt et al. | 73/64.43 |

FOREIGN PATENT DOCUMENTS

WO89/06803 7/1989 WIPO.

OTHER PUBLICATIONS

Patent Abstracts of Japan, vol. 9, No. 239, P-391 (1985).
Patent Abstracts of Japan, vol. 13, No. 138, P-852 (1988).

*Primary Examiner*—Hezron E. Williams
*Assistant Examiner*—Daniel S. Larkin
*Attorney, Agent, or Firm*—Steve T. Zelson, Esq.; James Harrington, Esq.

[57] ABSTRACT

A method for quantitation of blood parameters comprises the steps: provision of a sample of plasma, serum or blood, entering the sample into a cuvette with an internal dimension less than 1 mm, illuminating the sample by a light source, measuring and recording the changes of light properties caused by the sample as a function of time, calculating parameters of the recorded light signal/time curve such as slopes, extreme values, and the time distance between such extreme values, and interpreting the parameters as blood parameters. For the measurements, an apparatus is used comprising a cuvette (16, 17) with an internal dimension less than 1 mm, a light source (7, 9), means (8, 10) for measuring currently a light signal from the sample, means for recording the measured light signal values, and means for calculating parameters of the thereby defined light signal versus time graph.

19 Claims, 2 Drawing Sheets

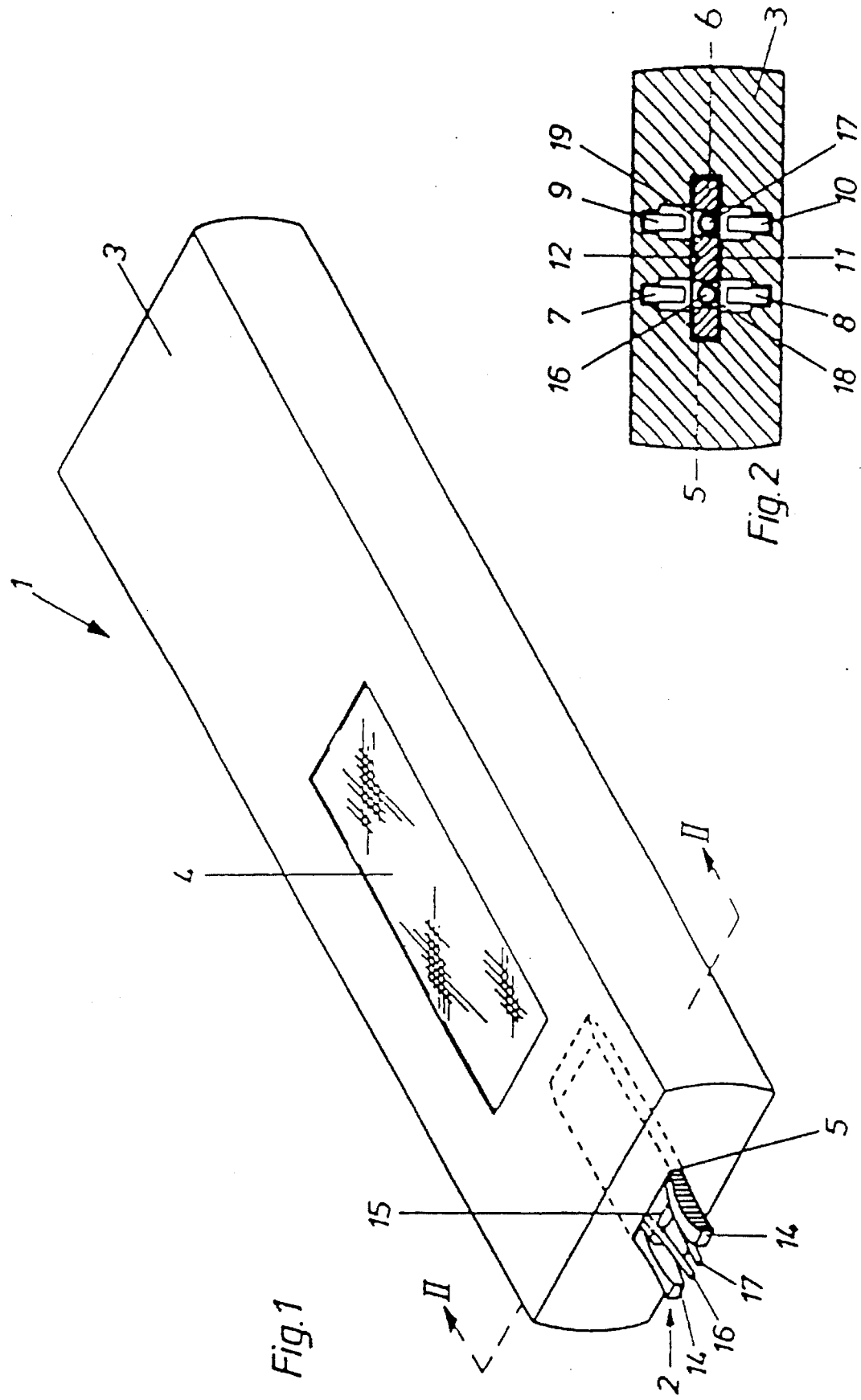

METHOD AND APPARATUS FOR QUANTITATION OF RELEVANT BLOOD PARAMETERS

CROSS-REFERENCE TO RELATED APPLICATIONS

This application is a continuation of PCT/DK92/00382 filed Dec. 18, 1992, the contents of which are incorporated herein by reference.

The provision of a blood sample for quantitation of various blood parameters is a routine procedure for many medical investigations. Commonly, a sample of some ml is taken and sent to a laboratory where the relevant parameters such as coagulation time, hematocit, sedimentation rate, hemoglobin percentage, etc are quantified.

To obtain a sample of some ml it is necessary to pass a cannula into a vein to make the necessary amount of blood flow into a vessel. The vessel must then be carefully labelled and sent to the laboratory wherefrom the determined data will issue later.

By this procedure the blood sample when taken has added to it an anticoagulant to prevent the blood from coagulating on its way to the laboratory. In the laboratory the effect of the anticoagulant is neutralized to make the sample equate a sample of fresh blood.

It is wanted to provide a method and an apparatus making it possible to decide the relevant parameters on the basis of fresh blood, the measuring beginning practically at the very moment the blood sample leaves the patient's body and being ended about 30 minutes later. The apparatus should be handy and portable to an extent making it possible to allocate the apparatus to the patient so that the blood sample may be passed into the apparatus, which may then be placed at the bedside until the result is ready. Further, the method should make it possible to perform the measurement on a blood sample which may be provided by simply pricking a finger or an earlobe to obtain a sample not larger than 25 µl, i.e. a sample which could be provided without help from a professional to puncture a vein.

A method of measuring the coagulation time for a blood sample is known, which method comprises the steps of entering the sample into a capillary element and measuring the coagulation time as the time elapsing from the moment when the blood sample enters the photometer measuring the translucence, which moment is indicated by a sudden fall of the translucence, until the moment when the translucence reaches a maximum after this sudden fall.

However, it has appeared that the development of the properties of light passing through or being scattered or reflected by a blood sample beyond the time of the occurrence of the first translucence maximum reveals interesting information of other relevant blood parameters.

According to the invention, a method for quantitation of relevant blood parameters comprises the following steps:

provision of a sample of plasma, serum or whole blood, entering the sample into a cuvette with an internal dimension less than 1 mm, illuminating the sample by a light source, measuring and recording the changes of light properties caused by the sample as a function of time, calculating parameters of the recorded light signal/time curve, interpreting the parameters such as slopes and time spaces between extremes and/or other well-defined points of the obtained light signal/time curve.

A light signal/time curve may have a course with a first sharp extreme value corresponding to the moment when the sample is introduced in the measuring part of the cuvette. If for example the light signal is the translucence of the sample, this extreme value is a minimum. From this minimum the translucence will rise to a maximum being the second extreme value from which it descends again to a relatively flat minimum representing a third extreme value, whereupon it rises again to a fourth extreme value, a high maximum from which it finally descends almost linearly.

The recording of the curve may be made by frequent storing, e.g. once a second, of connected values for measured light signal and time elapsed from a starting moment, mainly defined by the first sudden change in the light signal corresponding to the entering of the sample. These recordings make it possible to define the extreme values and to calculate slopes in different positions on the curve. However, when only the time elapsed between two incidents is needed, the recording of the intermediate light signal values may be omitted.

The time elapsing from the starting moment until a well-defined point in relation to the second extreme value is taken as an expression of the coagulation time.

The slope of the curve when passing from the first extreme value to the second extreme value may be taken as an expression of the sedimentation rate.

The difference between the first extreme value and the following second extreme value is taken as an expression of the haematocrit value.

The slope of the curve when passing from a well-defined point in relation to the second extreme value to a well-defined point in relation to the third extreme value is taken as an expression of the fibrinogen concentration and the platelet-related coagulation activity. As the slope of the curve varies, this value may be more precisely defined as e.g. the slope of its inflection, or the slope may be calculated as the difference between the second extreme value and a third extreme value or between well-defined points in relation to the extreme values divided by the time difference between these two extremes or points.

The time it takes for the light signal curve to pass the third extreme value is calculated as the time interval from the moment when the light signal value passes a set value differing by a predetermined amount from this third extreme value when approaching this value, until the moment when the light signal value passes again this set value after having passed the third extreme value, and this calculated time is taken as an expression of the activity of the fibrinolytic system.

The slope of the light signal curve when passing from a well-defined point in relation to its third extreme value to a well-defined point in relation to its fourth extreme value is taken as an expression of the rate of fibrin degeneration. The difference between the value in a well-defined point in relation to the third extreme value and a well defined point in relation to the fourth extreme value may be taken as an expression of the amount of fibrin in the sample and consequently of the original fibrinogen concentration.

If a reagent is added to the blood sample before the measurement is performed, this measurement will show how the blood parameters are influenced by the reagent.

An apparatus for performing the method according to the invention comprises a cuvette with an internal dimension less than 1 mm for receiving a blood sample, a light source for illuminating the sample, means for measuring the light signal from the sample in the cuvette, means for recording the measured light signal values, means for calculating the parameters of the recorded light signal versus time curve, and means for displaying the results of this calculation.

Appropriately, the calculation means may further convert the calculated curve values to clinical chemistry quantities.

The cuvette may be a capillary tube, and more cuvettes working in parallel may be provided each having its own measuring channel. This makes it possible to make a control on the measurement by taking it as an indication that the measurement should be rejected if the measuring results from the two parallel channels deviate by more than a preset value. Further, the use of more parallel cuvettes makes it possible to directly compare two samples, e.g one of the cuvettes may be coated by an active substance whereby a comparison of the samples in the two cuvettes gives an indication of the effect of the active substance.

The cuvettes may be disposable so that after use they may be removed from the apparatus and replaced by new ones. Also, the cuvettes may be mounted in an independent support piece which is designed to be accommodated in the apparatus and after use be removed from the apparatus and disposed of. The cuvettes mounted in the independent support piece may be capillary tubes which are so placed in the support piece that their inlet ends lie closely up against each other. This makes it possible to fill the two capillary tubes simultaneously from the same drop of blood.

The means for measuring the light signal from the samples may comprise a light source and a light sensor placed in a specific geometric relation to each other. The geometry is chosen with regard to which light signal should be measured. If translucence should be measured, connected light sources and sensors are placed opposite each other, whereas a measurement of scattered or reflected light is preferably measured by a sensor placed so that it would receive no light directly from the light source. It should be noticed that in the last mentioned case the light signal value is low when no sample is in the cuvette to reflect the light and will suddenly rise when the sample enters the cuvette.

According to the invention, the apparatus may comprise a microcomputer performing the recording of the light signal values by storing at preset time intervals the measured light signal values, performing the calculations of the curve parameters on the basis of the stored values, and translating the curve parameters into blood parameters.

The calculated parameters may be stored in the microcomputer and may be displayed on the display on request.

Figure 4:
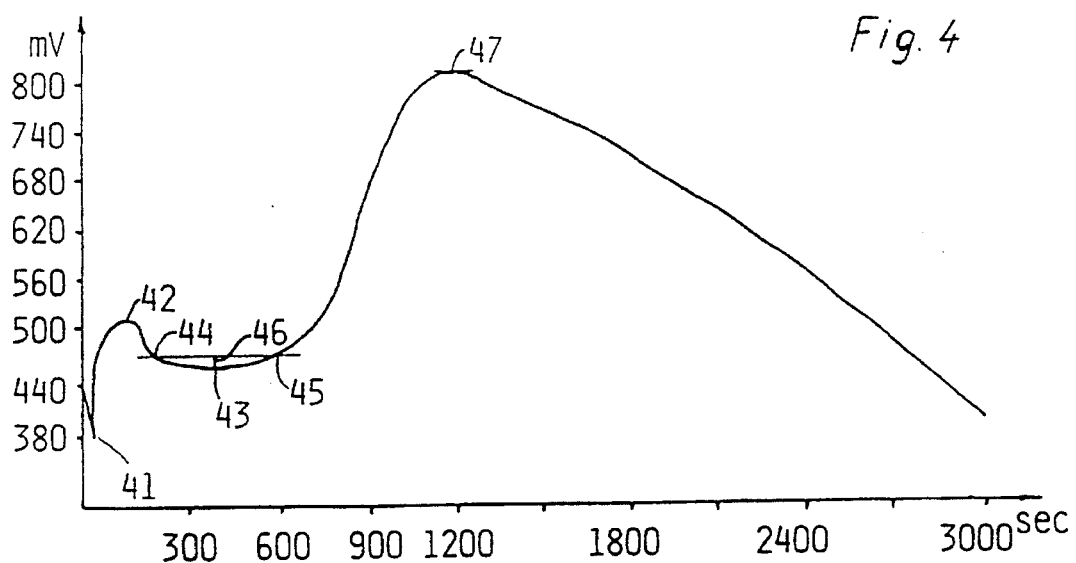

In the following the invention is described with reference to the drawing, in which FIG. 1 shows a perspective illustration of an embodiment of an apparatus with a support element with capillary elements inserted, FIG. 2 schematicly shows a cross-sectional view along the line II—II in FIG. 1, FIG. 3 shows the support element with the capillary elements during the filling of the capillary elements, FIG. 4 shows a translucence versus time curve for a blood sample.

The apparatus shown in FIG. 1 corresponds in its construction to the apparatus according to WO 89/06803 meant for determining the coagulation time for a blood sample. The apparatus itself is indicated as a whole by the reference number 1. It comprises a housing 3 with a display 4 on the one side. At one end of the housing 3 there is provided an opening 5 in which a support element carrying capillary elements may be inserted.

FIG. 2 illustrates how one or more light sources 7, 9, preferably in the form of light diodes, are mounted in the housing 3 in relation to the opening 5. Light meters, preferably in the form of photodiodes 8, 10, are mounted opposite the light sources 7,9 on the other side of the opening 5.

The apparatus is also provided with a not shown built-in microprocessor controlling the measuring sequence and calculating the blood parameters on the basis of the translucence measured and stored at preset time intervals. The apparatus only differs from the photometer apparatus according to the WO-application by the performances of the built-in computer which should be equipped with the necessary storage capacity and should be programmed to perform the necessary calculations and controlling. Further, the apparatus should be provided with means to call forward on request the stored and calculated data on the display, which display may further be designed to display not only digits but also curves.

FIG. 3 shows the support element 2 with two capillary tubes 16 and 17 during the filling of the tubes from a blood drop 21 provided by pricking a finger 20. The support element 2 comprises a support piece 6 which is preferably made from an opaque plastic. The one end of the support piece 6 is tapered to form a wedge 13 to ease the insertion in the opening 5 of the apparatus. The opposite end of the support piece 6 is provided with a pair of extensions 14 forming a finger grip for the handling of the support element. Moreover, the support element is provided with a groove 12 which together with a similar groove on the back side forms a guide for guiding the support element when inserted in the opening 5 of the apparatus. Finally, the support piece 6 is provided with a pair of windows 18 and 19, one behind each of the capillary tubes. These windows are placed so that they are in line with the light beam from the light source to the light sensor when the support element is inserted in the apparatus.

Although in the embodiment just described the capillary elements are described as being capillary tubes, other forms of capillary elements such as transparent sheets with a small distance between them may be used, just as the capillary elements may be individual and designed to be inserted into the apparatus directly without a supporting element. Also a single capillary element may be used, although two are preferred. The capillary elements may also be arranged so that blood sampling from venous tubes or a-v shunts is facilitated.

FIG. 4 shows a translucence versus time curve recorded during the coagulation sequence for a blood sample. The time elapsed is indicated as seconds along the X-axis, and the translucence is indicated as the output voltage in mV from the photo sensor.

When by the capillary effect the blood sample is sucked into the capillary element inserted in the measuring apparatus, it will cover the light beam through the window 18 or 19 when it reaches the part of the capillary element lying abreast of this window. Thereby the light sensed by the corresponding sensor will be damped suddenly, and a sudden fall will be seen on the translucence curve, illustrated at 41. From this minimum the translucence will slowly rise to a maximum 42, as by their gravity the blood cells are precipitated, and the translucent plasma collects above the precipitated substance. In this way the height of the maximum translucence following the first minimum is an indication of the hemacrit, i.e. the maximum 42 is related to the volume of blood cells in relation to the volume of the whole blood.

At the time for the first maximum the blood starts to coagulate and the translucence falls as the fibrin threads cause dispersion of light. The time from the first minimum 41 to the first maximum 42 defines in the known way the coagulation time.

From its first maximum the translucence falls until all fibrinogen is transformed into fibrin. From the minimum 43 hereby defined the translucence will rise again when the fibrinolytic system is activated. The slope of the falling curve may be taken as an indication of the fibrinogen concentration in the substrate. Also the height of the first maximum 42 over the second minimum 43 may be taken as an indication of the fibrinogen value, and unlike the above mentioned slope this indication is not influenced by a possible coating of the capillary element to stimulate the formation of fibrin.

After the passage of the second minimum 43 the fibrin is by the action of plasmin decomposed to fibrin split products, and the sample becomes more translucent. The second minimum is a rather flat one, and a measuring of the time passing from the moment when the translucence passes a value a preset distance 46 over the minimum 43 until the moment when it reaches the same value during the rising after the minimum may be taken as an indication of how quickly the fibrinolytic system may be activated, i.e. the velocity of transforming plasminogen into plasmin. The points on the translucence curve lying the preset distance 46 over the minimum 43 during the fall and the rise of the curve, respectively, are designated 44 and 45, respectively. As it is not possible to know at forehand the translucence value for the minimum, it is here necessary to look back into the recorded values when the appearance of the minimum is detected.

The slope of the curve for the rising translucence after the second minimum 43 is seen to be proportional with the plasmin concentration, and the height of a second maximum 47 over the second minimum 43 is related to the quantity of fibrin and consequently to the original fibrin concentration.

Having passed its second maximum value, the translucence falls almost linearly.

By recording the translucence at preset time intervals, data are stored making it possible to determine relevant parameters of the translucence/time-curve. In the computer such parameters may be translated into corresponding blood parameters. Another possibility is to make the computer display the curve directly, as many professionals would prefer to make their evaluation from a knowledge of the course of the curve. For others it may be sufficient to know that the different parameters should be maintained within certain intervals.

The determination of the slope of the curve may be made by differentiating. As the slope varies in time, it is necessary to decide what part of the curve should be used when determining this parameter. For the course from the first maximum to the second minimum and from the second minimum to the second maximum the slope of the curve may be determined as the slope of its inflection. The point of inflection may be found by differentiating the function twice.

Although in the example described the translucence of the sample is measured, it is within the scope of the invention to measure the light scattered or in any other way modulated by the presence of the sample. When measuring scattered light it is appropriate not to place the sensors opposite the light source but rather angularly displaced in relation to such a 180° position. Thereby it is avoided that the sensor receives light directly from the light source, and especially where a capillary tube is used advantage may be taken of the fact that the cylindric tube acts as a lens which may focus the light on the sensor.

It shall be noticed that the time spaces need not be defined as the time elapsing from one extreme value to the next one, but may be defined as the time space between points which are well defined in relation to these values.

We claim:

1. A method for quantitation of blood parameters, said blood parameters being coagulation time, sedimentation rate, hemocrit, fibrinogen concentration, platelet related coagulation activity, activity of the fibrinolytic system of the blood, rate of fibrinogen degeneration, amount of fibrin, and original figrinogen concentration, comprising the following steps:

(a) providing a sample of plasma, serum or whole blood;
   (b) entering the sample into a cuvette with an internal dimension less than 1 mm;
   (c) illuminating the sample by a light source;
   (d) measuring and recording the changes of light properties caused by the sample as a function of time to obtain a light signal versus time curve;
   (e) calculating parameters of the recorded light signal/time curve; and
   (f) interpreting the parameters as blood parameters.

2. A method according to claim 1, wherein the recording is made by frequently storing connected values for measured light signal and time elapsed from a starting moment for a measurement.

3. A method according to claim 1, wherein the time for a first extreme value caused by the introduction of the sample into the cuvette is interpreted as a starting moment for the measurement.

4. A method according to claim 1, wherein the time elapsing from a starting moment to a well defined point in relation to a second occurring extreme value is taken as an expression of the coagulation time.

5. A method according to claim 1, wherein the slope of the curve when passing from the first extreme value to a second extreme value is taken as an expression of the sedimentation rate.

6. A method according to claim 1, wherein the height of the curve when passing from the first extreme value to a second extreme value is taken as an expression of the hematocrit.

7. A method according to claim 1, wherein the difference between a second extreme value and a third extreme value is taken as an expression of the fibrinogen concentration.

8. A method according to claim 1, wherein the slope of the curve when passing from a second extreme value is taken as an expression of the fibrinogen concentration and platelet related coagulation activity.

9. A method according to claim 1, wherein the time it takes for the light signal curve to pass a third extreme value is calculated as a time interval from the moment when a light signal value passes a set value differing by a predetermined amount from this third extreme value when approaching this value, until the moment when the light signal value again passes this set value after having passed the third extreme value, and this calculated time is taken as an expression of activity of a fibrinolytic system.

10. A method according to claim 1, wherein the slope of the light signal curve when passing from a well-defined point in relation to its third extreme value to a well-defined point in relation to its fourth extreme value is taken as an expression of the rate of fibrin degeneration.

11. A method according to claim 1, wherein the difference between the value in a well-defined point in relation to a third extreme value and a well-defined point in relation to a fourth extreme value on the light signal curve is taken as an expression of fibrin in the sample and consequently of original fibrinogen concentration.

12. An apparatus for quantitation of blood parameters by performing the method according to claim 1, comprising
   (a) a cuvette with an internal dimension less than 1 mm for receiving a blood sample;
   (b) a light source for illuminating the sample;
   (c) means for measuring the light signal from the sample in the cuvette;
   (d) means for recording the measured light signal values;
   (e) means for calculating the parameters of the recorded light signal versus time curve; and
   (f) means for displaying the results of this calculation.

13. An apparatus according to claim 12, wherein the means for calculating further converts the calculated curve parameters to blood parameters.

14. An apparatus according to claim 13, wherein the cuvette is a capillary element.

15. An apparatus according to claim 14, wherein the cuvette is a capillary tube.

16. An apparatus according to clam 15, further comprising more parallel acting capillary tubes.

17. An apparatus according to claim 12, wherein the cuvette is mounted in a disposable part of the apparatus.

18. An apparatus according to claim 12, wherein the means for measuring the light signal comprises a light source and a light sensor facing each other on opposite sides of the cuvette.

19. An apparatus according to claim 12, further comprising a means for performing the current recording by storing at preset time intervals the measured translucence values, performing the calculations of the curve parameters on the basis of the stored values, and translating the curve parameters into blood parameters.

\* \* \* \* \*